US00PP08386P

United States Patent [19]

Akerboom

[11] Patent Number: Plant 8,386

[45] Date of Patent: Sep. 21, 1993

[54] ASTER PLANT NAMED PAINTED LADY

[76] Inventor: Petrus J. F. Akerboom, Paradijsweg 61, 2461 TL, Ter Aar, Netherlands

[21] Appl. No.: 895,623

[22] Filed: Jun. 9, 1992

[51] Int. Cl.[5] ..... A01H 5/00
[52] U.S. Cl. ..... Plt./68.1
[58] Field of Search ..... Plt./68.1

*Primary Examiner*—James R. Feyrer

*Attorney, Agent, or Firm*—Foley & Lardner

[57] ABSTRACT

A distinct cultivar of Aster plant named 'Painted Lady', characterized by its cupped capitulum form and daisy capitulum type, very light purple ray floret color, light yellow green disc florets, capitulum diameter of 33–35 mm, strong, well branched flower stems, and its numerous flowers borne on short pedicels.

1 Drawing Sheet

The present invention comprises a new and distinct cultivar of Aster L. hereinafter referred to by the cultivar name 'Painted Lady'.

'Painted Lady' is a product of a planned breeding program which had the objective of creating new perennial Aster cultivars for year-round commercial production having well branched flower stems, large flower (capitulum) size, good flower (capitulum) form and shape, and having superior vase-life lasting quality of the cut flowers. Such traits in combination were not present or needed improvement in previously available commercial cultivars.

'Painted Lady' was originated from a hybridization made by the inventor P. Akerboom in a controlled breeding program in Ter Aar, The Netherlands, in 1987. The female parent of 'Painted Lady' was an unnamed *Aster novi-belgii* seedling. The male parent was an unnamed *Aster novi-belgii* seedling.

'Painted Lady' was discovered and selected as one flowering plant within the progeny of the stated parentage by the inventor P. Akerboom on Sep. 10, 1987 in a controlled environment in Ter Aar and identified as seedling No. 87.M.K.B.R.3.G.

The first act of asexual reproduction of 'Painted Lady' was accomplished when vegetative cuttings were taken from the initial selection in November 1987 in a controlled environment in Ter Aar by a technician working under formulations established and supervised by P. Akerboom.

Horticultural examination of selected units initiated in 1988 and 1989 has demonstrated that the unique combination of characteristics as herein disclosed for 'Painted Lady' are firmly fixed and are retained through successive generations of asexual reproduction.

'Painted Lady' has not been observed under all possible environmental conditions. The phenotype may vary significantly under different environmental conditions of temperature, light intensity and daylength, without, however, any variance in the genotype.

The following observations, measurements and comparisons describe plants grown in Ter Aar, The Netherlands, under greenhouse conditions which approximate those generally used in commercial greenhouse practice in this country. The following traits have been repeatedly observed and are determined to be basic characteristics of 'Painted Lady', which, in combination, distinguish this Aster as a new and distinct cultivar:

1. Cupped capitulum form.

2. Daisy capitulum type.
3. Very light purple ray floret color.
4. Diameter across face of capitulum of 33 to 35 mm at maturity.
5. Strong, well branched flower stems.
6. Many capitula per synflorescence, borne on short pedicels.

The accompanying color photographic drawings show typical synflorescence of 'Painted Lady', with the colors being as nearly true as possible with illustrations of this type.

The top photograph is a perspective view of 'Painted Lady' grown as a single stem cut spray Aster.

The bottom photograph illustrates in top plan view several flowers of 'Painted Lady'.

Of the commercial cultivars known to the inventor, the most similar to 'Painted Lady' is the variety 'Pink Butterfly', disclosed in U.S. Plant Pat. No. 7,401. Reference is made to attached Chart A, which compares certain characteristics of 'Painted Lady' to the same characteristics of 'Pink Butterfly'.

In comparison to 'Pink Butterfly', 'Painted Lady' has more vigorous growth, thicker and courser flower stems, smaller leaves, larger flowers (capitula), a very light purple flower color compared to the soft red-purple or pink flower color of 'Pink Butterfly' and more numerous ray florets. Similar traits are capitulum form and type, spray formation, photoperiodic light reaction, and equally long lasting vase-lifes.

When compared to the male parent's flower and flower stem characteristics, 'Painted Lady' is much easier to handle during harvesting. *Novi-belgii* cultivars typically are brittle and have easy breaking flower heads and branching stems. 'Painted Lady' is absolutely free of these drawbacks.

In the following description color references are made to The Royal Horticultural Society Colour Chart. The color values were determined between 12:00 and 14:00 hours on Jun. 20, 1989 at Ter Aar, The Netherlands.

Classification:

*Botanical.*—*Aster pilosus*×*novi-belgii* cv 'Painted Lady'.

*Commercial.*—Medium, daisy-like spray Aster perennial.

INFLORESCENCE

A. Capitulum:

*Form.*—Cupped.

*Type.*—Daisy.

*Diameter across face.*—33 to 35 mm.

*Arrangement.*—Raceme inflorescence.

B. Corolla of ray florets:

*Color (general tonality from a distance of three meters).*—Light purple.

*Color (upper surface).*—Closest to 76D.

*Color (under surface).*—Closest to 76D.

*Shape of floret.*—Apex acute; very long, elliptic, straight.

*Size of floret.*—17–18 mm long×5 mm wide.

*Number of ray florets.*—30–38.

C. Corolla of disc florets:

*Color (mature).*—Closest to 1C/1D.

*Color (immature).*—Closest to 1C/1D.

*Diameter of disc.*—9–10 mm.

D. Reproductive organs:

*Androecium.*—Present on disc florets only; no pollen.

*Gynoecium.*—Present on both ray and disc florets.

PLANT

A. General appearance:

*Height.*—Tall; depends on light reaction; under continuous long days it can grow up to two meters tall; medium branching.

B. Foliage:

*Color.*—RHS 147A.

*Shape.*—Lanceolate to oblanceolate.

*Size.*—Lower leaves, length 135–140 mm, short to medium; width 25 mm, very broad. Upper leaves, length 110 mm, width 21 mm.

*Margin.*—Entire.

*Arrangement.*—Alternate, with angle acute.

CHART A
Comparison of 'Painted Lady' and 'Pink Butterfly'

| Cultivar | PAINTED LADY | PINK BUTTERFLY |
|---|---|---|
| Ray floret color | Very Light Purple | Light Pink |
| Capitulum form and type | Cupped daisy | Cupped daisy |
| Spray formation | Compound | Compound |
| Pedicels | 5–40 mm long | 7–12 mm long |
| Diameter across face of capitulum | 33–35 mm | 29–32 mm |
| Number of ray florets | 30–38 | 23–25 |

I claim:

1. A new and distinct cultivar of Aster named 'Painted Lady', as illustrated and described.

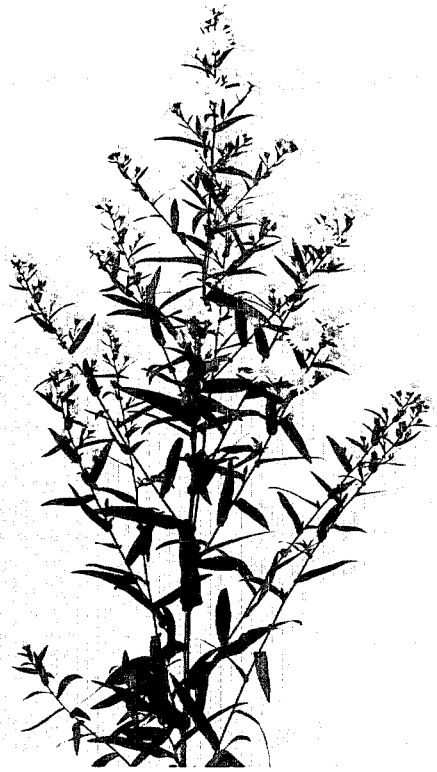
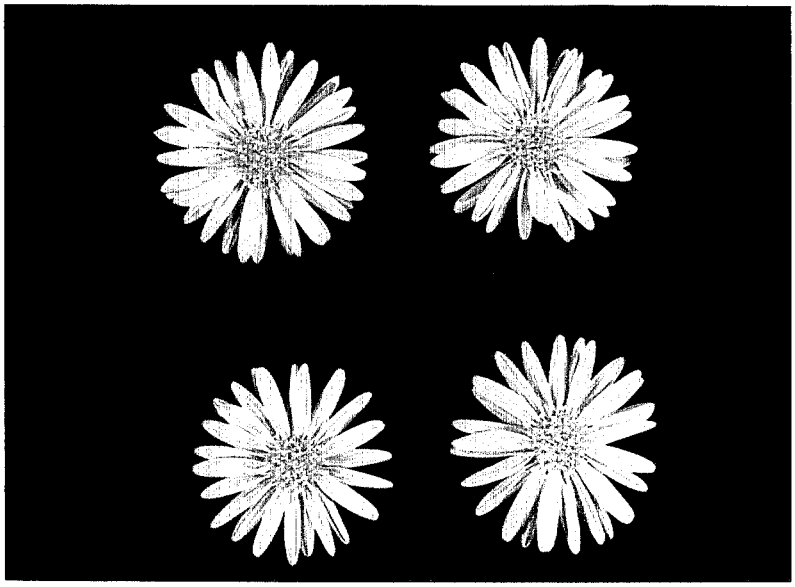

* * * * *